US009336585B2

(12) United States Patent
Zilberman (10) Patent No.: US 9,336,585 B2
(45) Date of Patent: May 10, 2016

(54) METHOD AND SYSTEM FOR DRAFTING A MAP FOR A "TUBE-SHEET"

(75) Inventor: Silviu Zilberman, Rishon Le-Zion (IL)

(73) Assignee: ACOUSTICEYE LTD, Tel Aviv (IL)

( * ) Notice: Subject to any disclaimer, the term of this patent is extended or adjusted under 35 U.S.C. 154(b) by 1175 days.

(21) Appl. No.: 13/332,873

(22) Filed: Dec. 21, 2011

(65) Prior Publication Data
US 2012/0162408 A1 Jun. 28, 2012

Related U.S. Application Data

(60) Provisional application No. 61/426,842, filed on Dec. 23, 2010.

(51) Int. Cl.
*G06T 7/00* (2006.01)
*G01N 21/956* (2006.01)
*G01N 21/88* (2006.01)

(52) U.S. Cl.
CPC ........ *G06T 7/0004* (2013.01); *G01N 21/95692* (2013.01); *G01N 2021/888* (2013.01); *G06T 2200/24* (2013.01); *G06T 2207/20096* (2013.01); *G06T 2207/30164* (2013.01)

(58) Field of Classification Search
CPC .................................................. G06T 7/0004
See application file for complete search history.

(56) References Cited

U.S. PATENT DOCUMENTS

| 4,729,423 | A | * | 3/1988 | Martin | F22B 37/003 165/1.1 |
| 4,891,767 | A | * | 1/1990 | Rzasa | B25J 9/1697 382/151 |
| 7,677,103 | B2 | | 3/2010 | Amir et al. | |
| 2013/0129166 | A1 | * | 5/2013 | Muller | B01D 21/262 382/128 |
| 2014/0204197 | A1 | * | 7/2014 | Olsson | H04N 5/23203 348/84 |
| 2014/0340505 | A1 | * | 11/2014 | Olsson | G01N 21/8803 348/84 |

* cited by examiner

*Primary Examiner* — Sath V Perungavoor
*Assistant Examiner* — James Pontius
(74) *Attorney, Agent, or Firm* — Smith Tempel; Gregory Scott Smith (57) ABSTRACT

A tester and a method that evaluate the condition of a bundle of plurality of tubes are disclosed. Embodiments of the tester obtains an image of a tube-sheet of the bundle; obtaining one or more parameters related to the tube-sheet image. Next one or more feature-detecting methods can be implemented on the tube-sheet image to define tube endings on a grid of the tube-sheet. Further, optimization methods can be implemented on the results and a map with the result can be presented to a user of the tester. Feedback from the user can be utilized to improve the map of the tube sheet.

19 Claims, 5 Drawing Sheets

Advance Tube Inspection Equipment (ATIE).

FIG. 1

Advance Tube Inspection Equipment (ATIE).

METHOD AND SYSTEM FOR DRAFTING A MAP FOR A "TUBE-SHEET"

CROSS-REFERENCE TO RELATED APPLICATIONS

This is a non-provisional application for patent being filed in the United States Patent Office under 35 USC 111 and 37 CFR 1.53(b) and claiming priority under 35 USC 119(e) to the provisional application for patent filed in the United States Patent Office on Dec. 23, 2010, bearing the title of METHOD AND SYSTEM FOR DRAFTING A MAP FOR A "TUBE-SHEET" and assigned Ser. No. 61/426,842, which application is incorporated herein by reference in its entirety.

FIELD OF THE INVENTION

The present invention relates generally to the field of non-destructive testing (NDT) systems and methods used in inspection of bundles of tubular objects and more particularly to automatically detecting tube ends and drafting a map of the tube-sheet.

DESCRIPTION OF BACKGROUND ART

When inspecting a bundle of similar tubes, such as those found in a heat exchanger, condenser, boiler etc., a map describing the tube layout must first be created. Normally the tubes terminate as openings in a large metal plate called a "tube-sheet". In order to present a report on the inspected tubes, a photo or diagram of the tube-sheet must be uploaded to a computer, on which problematic tubes can then be marked. Advanced tube inspection equipment uses this map also in order to help the technician operating the equipment synchronize the tube he is inspecting at each moment with this tube's location on the tube-sheet map.

When such a photo or diagram is uploaded into the computer, the actual tube endings must be marked on it, since the software must somehow be told where the tube endings are located. Current solutions involve doing this manually, using a computer mouse for example, therefore lengthy and error prone, since tube-sheets are sometimes composed of several thousand tube openings, or tube ending.

Figure 1:
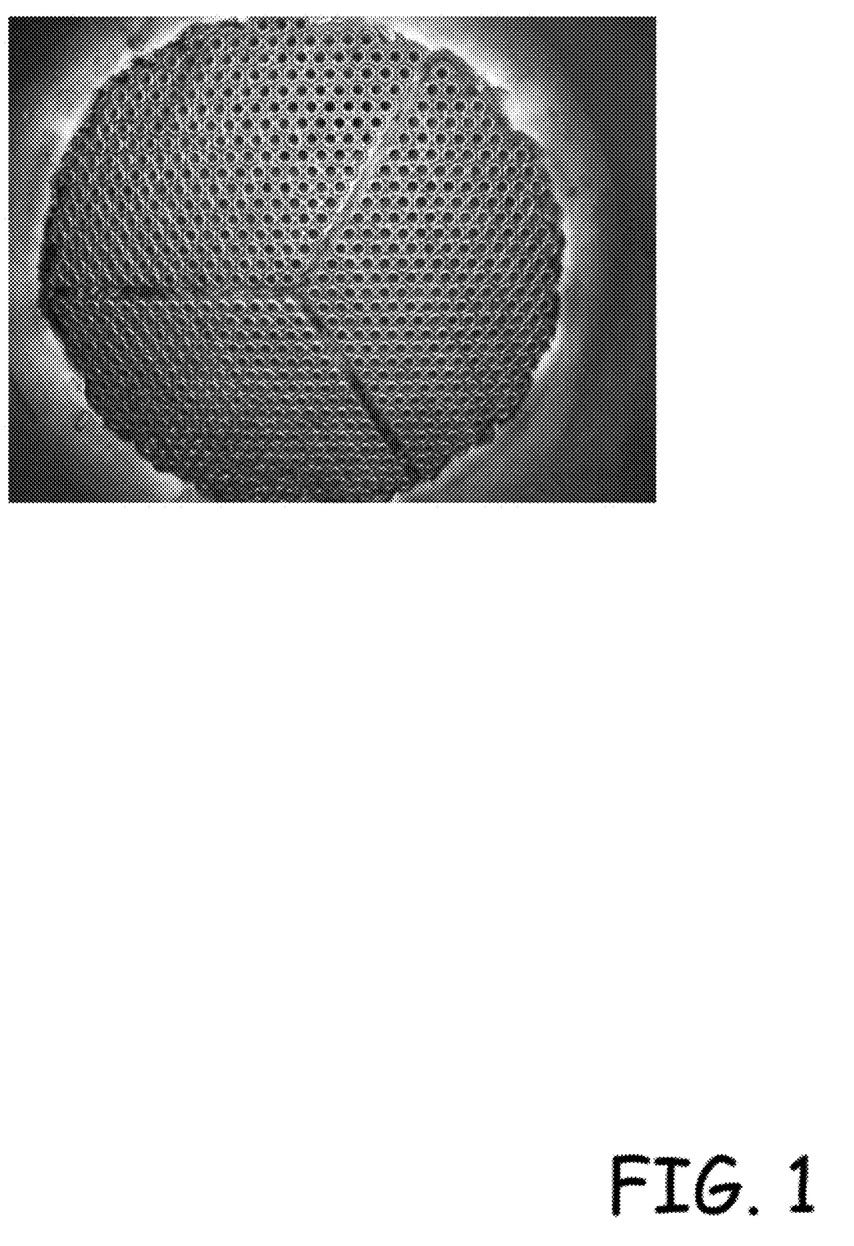
FIG. 1 is an exemplary image of a tube-sheet taken by a digital camera that illustrates the difficulties in analyzing the tube-sheet image.

Detecting the tube openings automatically is difficult. In the case where there is a schematic, it has often passed several rounds of photo copying; therefore the circles marking the tube ends are often faint and incomplete. In the case where this is a photo, the problem is much more difficult. Such photos are often, by necessity, taken from a short distance, facing the tube ends, using flash illumination. Therefore the tube end shapes are distorted, according to their angle from the camera, and the illumination is non-uniform. Tube endings far to the side can present themselves as darkened crescents instead of holes, whereas tube endings opposite the camera are strongly illuminated, with little shading, thus the round perimeter of the tube end might not be obvious. Such tubes and tube-sheets are often corroded and otherwise discolored, further complicating the detection. FIG. 1 illustrates an exemplary image of a common tube-sheet. As can be seen, the user had to take the image from a location that is right (from the observer side of the image) to the center of the tube-sheet and from a short distance. Consequently, the top right corner of the image is brighter than the edges; each section of the tube-sheet is differed from the others in the reflection, the shape of the opening of each tube, etc. . . .

SUMMARY OF THE DESCRIPTION

Therefore, there is a need in the art for a method for detecting the tube ends automatically, with as few errors as possible.

Different embodiments of the present invention solve the above-described needs by using a common camera, even a camera of a cellular phone, loading the image from the camera into a processor such as but not limited to a personal computer, a laptop, notebook, PDA, etc. At this point of time the processor starts processing the information in interaction with an operator. In some embodiments additional information can be added manually before starting the automatic process. Information such as pointing on two points on the circumference of a tube in order to indicate the diameter of a tube out of the plurality of similar tubes. Yet in some embodiments addition information can be marked on the image in order to mark a region of interest (ROI) that bound the bundle of similar tubes, etc.

In one exemplary embodiment the processor can be the processor of an advanced tube inspection equipment (ATIE). An exemplary ATIE can be based on Acoustic Pulse Reflectometry (APR) measuring system. An exemplary APR system for Non-Destructive Testing (NDT) of tubular systems has been described in detail in a U.S. Pat. No. 7,677,103 which has been incorporated herein by reference. Other NDT methods that can use such tube sheet mapping can be based on Eddy Current technology (ECT); videoscope imaging etc.

After loading the image into the processor, the processor can prompt the operator to indicate, by various means (mouse clicks, for example), the diameter or circumference of a single tube end and/or a sub-picture containing a single tube; and the border lines of the tube-sheet; etc. The processor may apply contrast enhancement and then searches for patterns resembling circles (or ellipses) of such a diameter (within some tolerance range), based on incomplete contours, in different lighting conditions. Some methods allow some degree of distortion in the shape of the openings, since tube ends that are far off the axis of the camera appear distorted.

Then, embodiments of the detecting method may employ various methods of image processing such as but not limited to, feature detection, correlation or shapes detection. However most standard methods are of limited success due to the above mentioned objective difficulties associated with non-uniform image quality and photographic conditions. Some methods employ various tunable parameters that may dramatically improve the detection results, and the common prior art method to determine those parameters is by trial-and-error. Some of them can prompt the user to modify certain parameters until satisfactory results are obtained. However this is a slow and cumbersome procedure and is very sensitive to the technical skills of the operator.

The present disclosure teaches exemplary methods for optimal selection of those tunable parameters without any user intervention. An exemplary embodiment transforms the tube detection problem into an optimization problem, where the tunable parameters are selected such that some objective function is minimized or maximized. These objective functions may include, but are not limited to, maximizing the number of detections of tube ending, maximizing the average correlation, minimizing the number of false detection, etc. The procedure may also lead to false positive detections. False positive detections could be identified and removed by taking advantage of the regular grid structure that is typically formed by the tubes holes in the tubes-sheet image. A similar method can be applied to detect false negatives (misdetections) by looking for vacancies in the grid structure. One exemplary way to analyze false positive or negative detections can be by implementing various statistical and geometrical methods that comply with regular features of a grid and remove detections that do not adhere to the regular grid structure. The features include, but not limited to, identifying basis vectors of the grid, pair correlation functions, geometrical outlier and other measures.

The foregoing summary is not intended to summarize each potential embodiment or every aspect or feature of the various embodiments of exemplary embodiments of advanced tube inspection equipment (ATIE) implementing tube-sheet analyzing methods, and other features and advantages will become apparent upon reading the following detailed description of the embodiments with the accompanying drawings and appended claims.

Furthermore, although specific exemplary embodiments are described in detail to illustrate the inventive concepts to a person skilled in the art, such embodiments can be modified to various modifications and alternative forms. Accordingly, the figures and written description are not intended to limit the scope of the inventive concepts in any manner.

Other objects, features, and advantages of the present invention will become apparent upon reading the following detailed description of the embodiments with the accompanying drawings and appended claims.

BRIEF DESCRIPTION OF THE DRAWINGS

Exemplary embodiments of the present disclosure will be understood and appreciated more fully from the following detailed description, taken in conjunction with the drawings in which.

DETAILED DESCRIPTION OF DIFFERENT EMBODIMENTS

Turning now to the figures in which like numerals represent like elements throughout the several views, exemplary embodiments of the present invention are described. For convenience, only some elements of the same group may be labeled with numerals. The purpose of the drawings is to describe exemplary embodiments and not for production. Therefore features shown in the figures are chosen for convenience and clarity of presentation only.

FIG. 1 is illustrates an image 100 of a tube-sheet taken by a digital camera to be used by an exemplary embodiment of the present disclosure. The image demonstrates some of the difficulties in analyzing the tube-sheet image in order to define a map of its tube-sheet.

Figure 2:
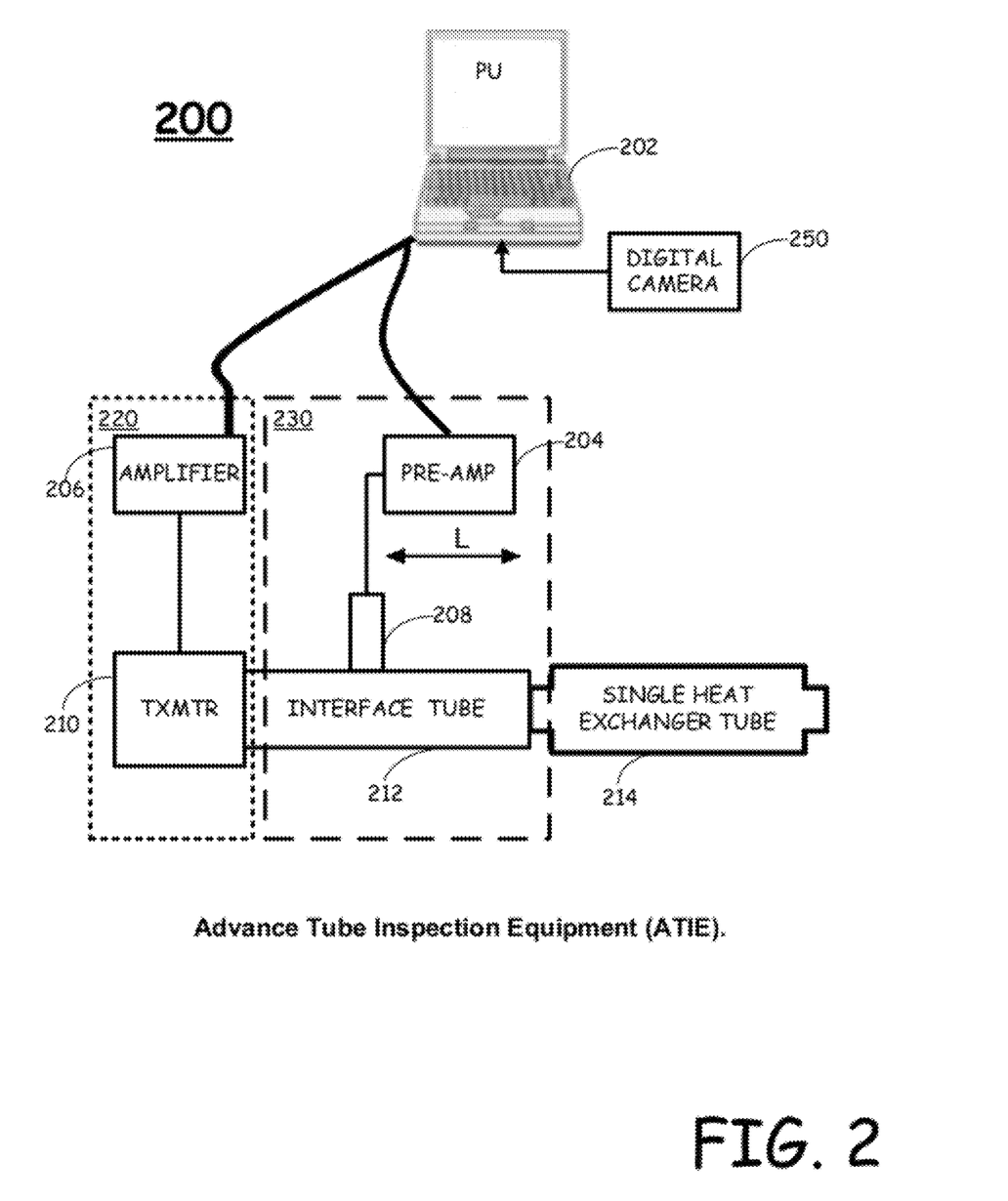
FIG. 2 is a simplified block diagram with relevant elements of an exemplary advanced tube inspection equipment (ATIE) system which implements exemplary techniques of the present disclosure.

FIG. 2 illustrates an exemplary block diagram with relevant elements of an exemplary embodiment of an advanced tube inspection equipment (ATIE) 200 for measuring and evaluating the condition of a bundle of tubes by implementing automatic mapping of the tube-sheet of the bundle and using APR technology for measuring the condition of one or more tubes of the bundle. The illustrated hardware components of the ATIE are configured to provide Non Destructive Testing (NDT). It should be noted that the configuration illustrated in FIG. 2 is used for illustration purposes only and therefore is not shown to any particular scale and the illustrated functional boundaries are not absolutely necessary in the actual implementation of the measuring system. For example, the length of an interface tube 212 can be shorter, longer or the same as the length of an exchanger tube 214. The exemplary ATIE 200 is based on APR as an example technique. The disclosed automatic mapping processes of the tube-sheet are not limited to APR system. Other embodiments of ATIE can be based on Eddy Current method, ultrasonic method, videoscope imaging, etc.

The illustrated embodiment 200 includes a signal injector 220 and a signal detector 230. It should be understood that the term signal and wave is used interchangeably in this description and encompasses any form of energy that can be propagated through the tube and reflected and detected. The signal injector 220 is configured to inject a signal into a medium, or interface tube 212, which acts as an interface to the target structure being tested 214. The signal injector 220, the signal detector 230 and the interface tube 212 can be embedded in an assembly that can be referred as a measuring probe. The measuring probe can be carried by the user that performs the measuring and be attached to each tube under test. The signal detector 230 includes a sensor 208 that detects signal reflected back from the target structure 214 into the interface tube 212. The signal injector 220 and signal detector 230 may operate as a stand-alone unit, a stand-alone unit that interfaces and/or reports information to other system, a support unit that is controlled by an external processing unit 202, as well as other structures and/or configurations. For instance, in the stand-alone configuration, the processing unit may be incorporated into the signal injector 220 and/or the signal detector 230. In such embodiments, the processing unit 202 may be as simple as a microcontroller, an ASIC or even simply analog and/or digital control circuitry. The stand-alone unit may include a user interface for initiating a test sequence or, it may simply be activated by coupling the interface tube 212 to a structure under test 214. The recorded signal may be stored in internal memory and/or information regarding the detection may be displayed to a user in a variety of manners including the use of an LCD or even simple codes displayed using lights or numbers, or audible sounds such as error codes or certain tones or buzzers may also be used.

In the illustrated embodiment, the signal injector 220 is coupled to the processing unit 202 and the structure under test 214. The signal detector 230 is coupled to the processing unit 202 and the structure under test 214.

More specifically, in the illustrated ATIE 200 processing unit 202 synthesizes an acoustic pulse which is transmitted through a transmitter 210 via an amplifier 206. Thus, the processing unit 202 may include a signal generator or, a signal generator can be external to the processing unit 202, such as in the signal injector 220 or in-line between the processing unit 202 and the signal injector 220. The signal is converted into an acoustic wave by TXMTR 210, which can be a loudspeaker or similar transducer. The acoustic wave first propagates down an interface tube 212, where it can be detected and/or recorded by a sensor, such as a pressure sensor 208. Sensor 208 may be a transducer, a microphone or any of a variety of other devices that can detect acoustic waves. The acoustic wave can be a pulse of an acoustic wave for example, that travels down the structure 214, the current target tube from the bundle of a plurality of tubes, which is being examined. Any change in cross section of the target tube 214 will cause a reflection that will propagate back up the structure 214 and the interface tube 212, to be recorded by the pressure sensor 208, amplified by a pre-amp 204 and stored in the computer 202. The recorded reflections are analyzed in the computer 202 in order to identify the types and or severity of the faults that caused or resulted in creating the reflections. As non-limiting examples, the faults may be blockages (full or partial), pitting, erosion, cracks, kinks, bulges and holes. It will be appreciated that in some embodiments, multiple interface tubes can be utilized with each having a pressure sensor 208 but being fed by the same transmitter. In such embodiments, multiple structures can be tested at the same time or in consecutive fashion. A reader who wishes to learn more about an APR system is invited to read U.S. Pat. No. 7,677,103 which has been incorporated herein by reference.

In addition to the above component ATIE 200 further comprises a digital camera 250. The digital camera can be any common digital camera that can deliver digital images to processing unit 202. Exemplary cameras can be manufactured by a plurality of companies such as but not limited to Olympus, Kodak, etc. In some cases a common cellular phone with a camera can be used as camera 250. The data from the camera 250 can be transferred to the computer by using different methods, such as but not limited to USB connection; wireless connection based on Bluetooth protocol; transferring a memory card, which stores the digital image, from the camera to the processing unit 202; etc.

Figure 3A:
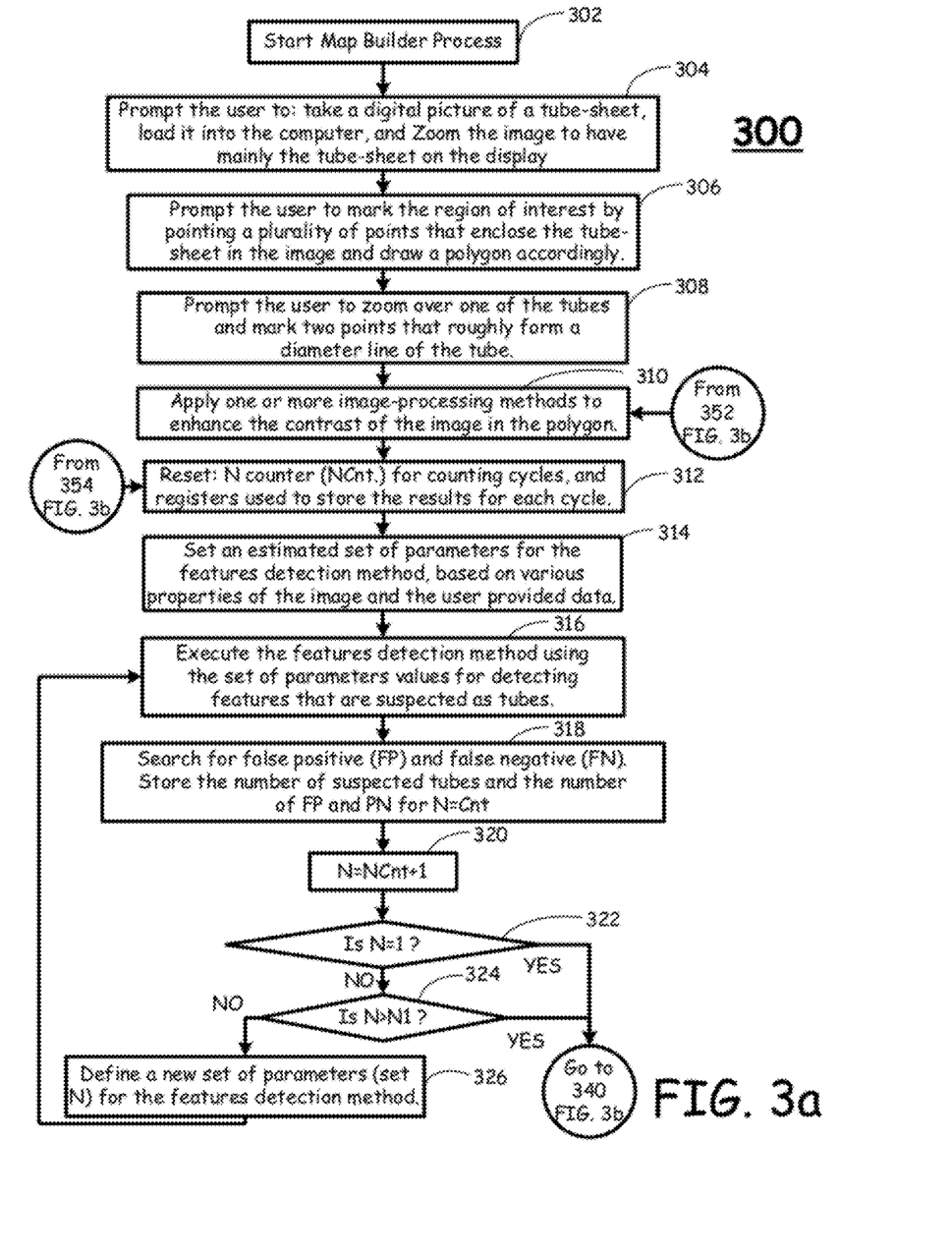
FIGS. 3a&b illustrates a flowchart showing relevant actions of an exemplary process of mapping a tube-sheet from an image.
Figure 3B:
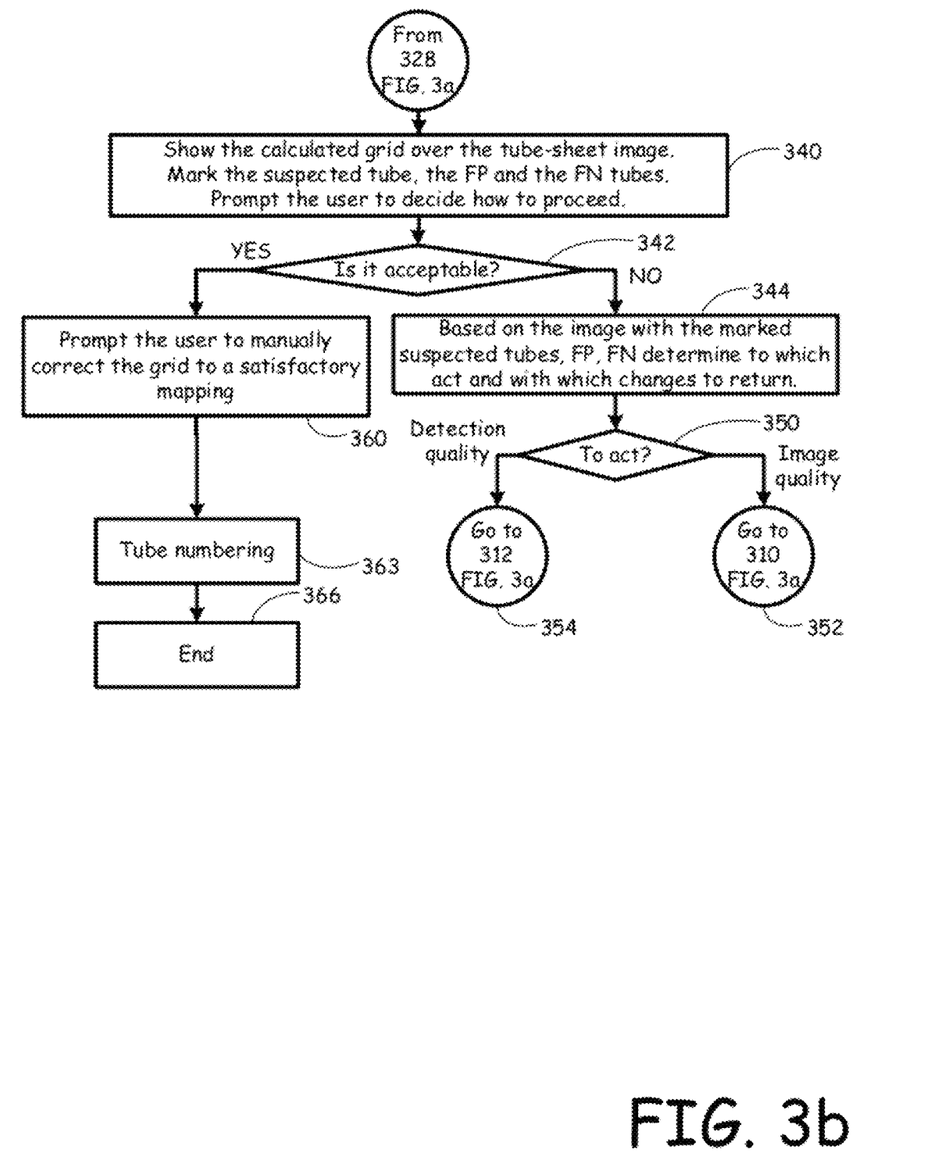

Referring now to FIGS. 3a and 3b that illustrate relevant actions of an exemplary tube-sheet map drawing process 300 that can be implemented by an exemplary ATIE such as but not limited the ATIE 200 that is disclosed above in conjunction with FIG. 2. At the beginning of the process, processing unit (PU) 202 can prompt 304 the user to take a digital picture of the relevant tube-sheet, for example tube-sheet 100 (FIG. 1). The image can be taken by a digital camera such as camera 250 (FIG. 2). At block 304 process 300 may further prompt the user to load the image to PU 202, to zoom it up and move the image until the tube-sheet image covers most of the display of PU 202. Prompting the user can be done by audio messages or by presenting text messages on the display of PU 202. In some embodiments, both methods can be implemented.

After the tube-sheet is presented over the display, the user is prompted to mark 306 the region of interest (ROI) by pointing a plurality of points along the circumference of the tube-sheet image. After pointing the plurality of points, method 300 may automatically drawn a polygon that connects those points and surrounds the tube-sheet. In some embodiments the user can be prompted to check the quality of the polygon and the user can modify the polygon in order to cover missing tubes or removes irrelevant areas out of the polygon.

At block 308 the user can be prompted provide some data about the tube-sheet. For example, the user can be requested to zoom up around one of the tubes and to point two points on the circumference of the tube that the distance between them is similar to the diameter of the tube. In some embodiments the user may be prompted to point the diameter of several tubes in order to use an average value of the diameter, etc. Yet in some embodiments the user may be prompted to provide additional data about the tube-sheet. Data such as but not limited to the number of tubes in the bundle, the pitch between tubes in a row, the pitch between rows, etc.

After obtaining the user provided data, process 300 may start implementing several automatic actions. PU 202 (FIG. 2) may start 310 by implementing one or more image-processing methods for improving the quality of the image and to facilitate the automatic mapping. Exemplary image processing methods can include image enhancement methods, such as but not limited to: linear and non-linear filtering, such as finite impulse response (FIR) and median filters; Global and local contrast enhancement in the region of interest, e.g. by remapping the pixel values to a wider scale, etc. Some embodiments of process 300 may implement image processing methods only in the interesting area of the image that is limited inbetween the polygon which was drawn in block 306. At this point, after improving the image, the automatic mapping process can be initiated.

At block 312, process 300 resets an 'N' counter (NCnt) that counts the number of optimization cycles that will be implemented in order to achieve an improved mapping of the tube-sheet. In addition several registers are reset. Those registers can be used for storing the results of each optimization cycle to enable comparing the results of the cycles and controlling the optimization process.

A set of parameters for the features-detection methods is defined 314 by defining the properties of the image and the user provided data. The properties of the image may include: brightness gradients, contrast, dark point value, white point value, etc. Those properties of the image can be concluded by processing the raw data of the image. The user provided data may include: the diameter of a tube, the interesting area which is limited by the polygon, etc. The defined set of parameters may include parameters such as but not limited to: tolerances of the diameter or the main axes of ellipses, typical brightness gradients inside and in the near vicinity of tube endings etc.

After obtaining the required parameters and properties in block 314 one or more features-detecting methods can be implemented 316 in the interesting area of the improved image of the tube-sheet. The feature-detecting methods can be tuned to search tube ending. Exemplary features-detecting methods can comprise: boundary tracking for domain identification; Correlation between a tube-ending sample and the rest of the image; Circular/elliptical Hough transform; and Quad-tree decomposition, etc. At the end of block 316 features that are suspected as tube-endings can be marked, counted and the number of suspected tubes can be stored at one of the registers.

At block 318 process 300 may search for false positive (FP) and false negative (FN) detections. Searching for FP and/or FN can be done by processing geometrical features of the detected bundle of suspected tubes. The suspected tubes can be placed on a calculated grid. The geometrical features of the grid can be the pitch between tubes in a row, the pitch between rows, an average diameter, etc. An exemplary process 300 can estimate the location of each tube in the calculated grid. A suspected tube that is not located on a point of the calculated grid can be assumed as FP. A point on the calculated grid that does not include a suspected tube can be assumed as FN. The FP and the FN tubes can be marked too. Each number of the FN and FP tubes can be store in one of the registers. The three registers that store the number of suspected tubes, FN and FN tubes can be related to cycle 'N', wherein 'N' is equal to the current value of NCnt.

Yet in an embodiment method 300 can be executed two or more times using different feature-detecting methods. Then, the results of the two methods can be compared and identified tubes that are marked only by one of the methods can be marked as suspected tube.

At block 320 'N' is incremented by one, and a decision is made 322 whether N is equal to one, the first and initial optimization cycle, if yes, then method 300 proceeds to block 340 in FIG. 3b. If 'N' is not one, then a decision is made 324 whether 'N' is greater than N1. N1 can be any positive integer number. A preferred value of 'N1' can be in the range of five to fifteen cycles, for example. If 'N' is greater than N1, then method 300 proceeds to block 340 in FIG. 3b. If 324 'N' is not greater than N1, then process 300 proceeds to block 326 for defining a new set of parameters for the feature-detection method to be used in the next cycle.

The results of the current cycle of executing the one or more feature detection methods, the number of suspected tubes, FP and FN tubes, can be compared to the stored results of the previous one or more cycles. Based on the trend of the values of one or more objective functions and in order to maximize or minimize the one or more objective functions, a new set of parameters for the feature detection method can be defined at block 326. Exemplary objective functions can comprise: maximizing the number of detections of tube ending, maximizing the average correlation, minimizing the number of FP and or FN detection, etc. In some embodiments two or more objective functions can be used.

After defining 326 the new set of parameters (set 'N') for the feature-detection method, process 300 can return to block 316 and start a new cycle of defining the location of the tube-endings in the tube-sheet image.

Referring now to block 340 in FIG. 3b. Block 340 is implemented after the first cycle and after the N1 cycle of executing the features-detection method. In this section the user involvement can be needed. At block 340 the calculated grid is placed over the image of the tube-sheet as a map of the tube-sheet. In this map the suspected tube-endings can be marked by a certain color, FN tube-endings can be marked by another color and FP tube-endings can be marked in a third color. Then, the user can be invited to evaluate the automatic mapping results.

At block 342 a decision is made, by the user, whether the presented mapping is acceptable. The decision can be based on the amount of the corrections that the user has to do manually. If 342 the mapping is acceptable, then the user is prompt 360 to correct the presented map (grid) over the tube-sheet image. The correction may include: deleting FP tubes, adding FN tubes etc. When the map reaches the satisfactory of the user, the user can send an indication to PU 202 (FIG. 2) and process 300 can proceed to block 363.

At block 363 a tube marking process can be implemented. In one embodiment the numbering can be done manually, the user give a number to each tube in the map. In other embodiment the numbering can be done automatically. Process 300 can move from top left tube in the map to bottom right tube, moving from left to right in row and moving down row after row. In another embodiment a semi-automatic process can be implemented, in such a process the user can define the beginning of each row and the PU 202 (FIG. 2) can proceed and numbering the tubes in that row. Other embodiments may use other numbering methods.

After giving numbers to each tube in the map, method 300 can be terminated 366 and PU can prompt the user to start inspecting of the condition of one or more tubes (by pointing to the tube on the map) that has to be measured by the ATIE.

Returning now to block 342, If at block 342 the user determines that the presented map is not acceptable, then at block 344 the user is prompted to observe the image and the calculated map and determine which act can improves the automatic mapping. The reasons for rejecting the presented map can be such but not limited to: too many FN or too many FP. If 350 the image quality is poor, then the user may instruct the PU 202 to return 354 to block 310 in FIG. 3a and to restart the process from the action of applying one or more image-processing methods. In some embodiments, the user may be prompted to select one or more image processing methods from a menu that is presented to the user. Yet in another embodiment the user may return to block 304 and shot another image of the tube-sheet and may start the process again. Alternatively the user may use the image and may define manually certain tubes or parameters, etc.

If 350 the features-detection quality was poor while the image quality is OK, then, the user may instruct 352 the PU 202 to return to block 312 in FIG. 3a and to restart the process from the action of reset the NCnt and the different registers. In some embodiments, the user may be prompted to redefine one or more elements from the user provided data, from a menu that is presented to the user. Base on the quality of the map the user may define certain properties, such as a new setting of the diameter, adding pitch information, etc.

Figure 4:
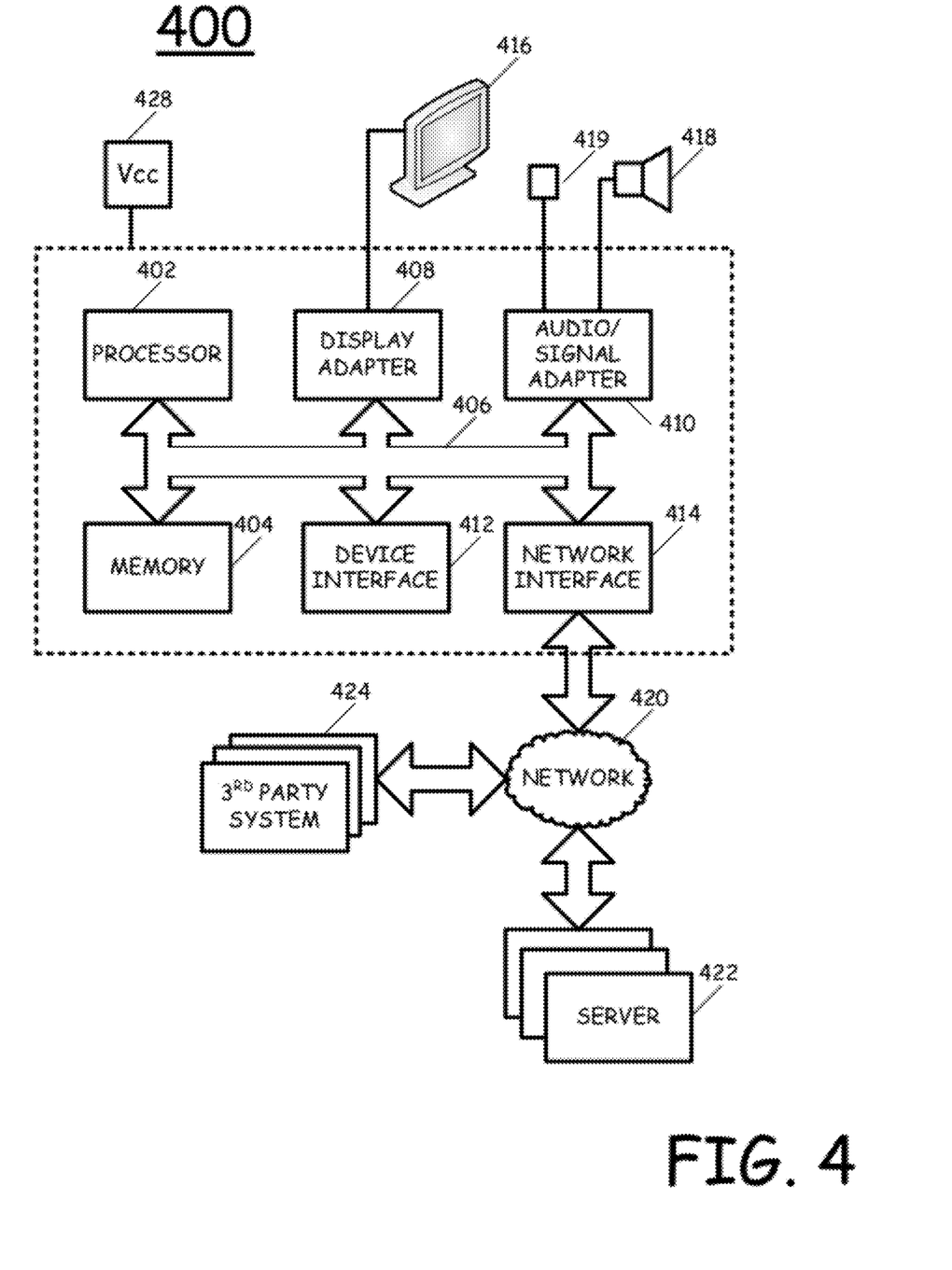
FIG. 4 is a functional block diagram of the components of an exemplary embodiment of the measuring system, as well as other embodiments thereof.

FIG. 4 is a functional block diagram of the components of an exemplary embodiment of the PU 202 (FIG. 2), as well as other embodiments thereof. It will be appreciated that not all of the components illustrated in FIG. 4 are required in all embodiments of the PU 202 but, each of the components are presented and described in conjunction with FIG. 4 to provide a complete and overall understanding of the components. Further, many specific elements are not presented in FIG. 4 but rather functions and/or functional interfaces are used in a generic fashion to indicate that various embodiments may use a variety of specific components or elements. The ATIE 200 (FIG. 2) can include a general computing platform 400, which is illustrated as PU 202 (FIG. 2), illustrated as including a processor 402 and a memory device 404 that may be integrated with each other (such as a microcontroller) or, communicatively connected over a bus or similar interface 406. The processor 402 can be a variety of processor types including microprocessors, micro-controllers, programmable arrays, custom IC's etc. and may also include single or multiple processors with or without accelerators or the like. The memory element of 404 may include a variety of structures, including but not limited to RAM, ROM, magnetic media, optical media, bubble memory, FLASH memory, EPROM, EEPROM, internal or external-associated databases, etc. The processor 402, or other components may also provide components such as a real-time clock, analog to digital converters, digital to analog converters, etc.

The processor 402 also interfaces to a variety of elements including a control or device interface 412, a display adapter 408, audio/signal adapter 410 and network/device interface 414. The control or device interface 412 provides an interface to external controls or devices, such as sensor, actuators, transducers or the like. The device interface 412 may also interface to a variety of devices (not shown) such as a keyboard, a mouse, a pin pad, and audio activate device, as well as a variety of the many other available input and output devices or, another computer or processing device. The device interface may also include or incorporate devices such as sensors, controllers, converters, etc. For instance, the amplifier 206, the transmitter 210, and the preamp 204 illustrated in FIG. 2 could all be included in the device interface 412 either as internal or integrated components or, the device interface 412 may interface to the devices as external components.

Alternatively the processing unit 202 illustrated in FIG. 2 could interface to the measuring elements as a stand-alone third party system through control lines, a wired network or a wireless network. The display adapter 408 can be used to drive a variety of alert elements and/or display devices, such as display devices including an LED display, LCD display, one or more LEDs or other display devices 416. The audio/signal adapter 410 interfaces to and drives another alert element 418, such as a speaker or speaker system, buzzer, bell, etc. In the various embodiments of the measuring device, the audio/signal adapter 410 could be used to generate the acoustic wave from speaker element 418 and detect the received signals at microphone 419. The amplifiers, digital-to-analog and analog-to-digital converters may be included in the processor 402, the audio/signal adapter 410 or other components within the computing platform 400 or external there to. The network/device interface 414 can also be used to interface the computing platform 400 to other devices through a network 420. The network may be a local network, a wide area network, wireless network, a global network such as the Internet, or any of a variety of other configurations including hybrids, etc. The network/device interface 414 may be a wired interface or a wireless interface. The computing platform 400 is shown as interfacing to a server 422 and a third party system 424 through the network 420. A battery or power source 428 provides power for the computing platform 400.

Overall, embodiments of ATIE that are disclosed above will reduce the time of measuring the condition of a bundle of a plurality of tubes, reduces mistakes in boring process of mapping a tube-sheet with a plurality of tubes.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

In this application the words "unit", "element" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware. Software of a logical module can be embodied on a computer readable medium such as a read/write hard disc, CDROM, Flash memory, ROM, etc. In order to execute a certain task a software program can be loaded to an appropriate processor as needed.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Many other ramification and variations are possible within the teaching of the embodiments comprising different combinations of features noted in the described embodiments.

It will be appreciated by persons skilled in the art that the present invention is not limited by what has been particularly shown and described herein above. Rather the scope of the invention is defined by the claims that follow.

What is claimed is:

1. An advance tube inspection equipment (ATIE), comprising:
   a processor;
   a measuring probe; and
   a digital camera;
   wherein the digital camera captures an image of a tube-sheet of a bundle of a plurality of tubes and loads the image of the tube-sheet to the processor;
   wherein the processor analyzes the image of the tube-sheet received from the digital camera and defines a map with a location of one or more tubes over the tube-sheet image; and
   wherein the measuring probe, based on the defined map, is associated with one or more tubes in the bundle of the plurality of tubes and transmits and receives measuring signals to and from a currently associated tube, converts the received measuring signals into electronic measuring signals and transfers the electronic measuring signals toward the processor.

2. The ATIE of claim 1, wherein the processor uses the map for controlling the association of the measuring probe with a next tube to be measured.

3. The ATIE of claim 1, wherein the processor analyzes the tube-sheet image data received from the digital camera comprises applying one or more image-processing methods on the imaged before defining the map.

4. The ATIE of claim 3, wherein the one or more image-processing methods comprises contrast enhancement.

5. The ATIE of claim 1, wherein the processor analyzes the tube-sheet image data received from the digital camera by applying one or more feature-detecting methods for defining the map.

6. The ATIE of claim 5, wherein the one or more feature-detecting methods comprises boundary tracking for domain identification method.

7. The ATIE of claim 5, wherein the one or more feature-detecting methods comprises correlation between a tube-ending sample and a rest of the image.

8. The ATIE of claim 5, wherein the one or more feature-detecting methods comprises circular/elliptical Hough transform.

9. The ATIE of claim 5, wherein the one or more feature-detecting methods comprises quad-tree decomposition.

10. The ATIE of claim 5, wherein the processor analyzes the tube-sheet image data received from the digital camera further by optimizing a results received from the features-detecting method to reach an objective function.

11. The ATIE of claim 10, wherein the objective function minimizes a number of false positive detections.

12. The ATIE of claim 10, wherein the objective function maximizes an average correlation.

13. The ATIE of claim 10, wherein the objective function maximizes a number of detections of tube endings.

14. The ATIE of claim 10, wherein the objective function minimizes a number of false negative detection.

15. The ATIE of claim 5, wherein the processor obtains one or more parameters about the tube-sheet that are used by the one or more feature-detecting methods.

16. The ATIE of claim 15, wherein the one or more parameters include information on a diameter of a tube in the tube sheet image.

17. The ATIE of claim 15, wherein the one or more parameters include information on a grid of the tube sheet image.

18. The ATIE of claim 17, wherein the information on the grid of the tube sheet includes pitch information.

19. The ATIE of claim 15, wherein the one or more parameters include region of interest over the tube sheet that defines an area in the tube-sheet image to be covered by the map.

* * * * *